United States Patent [19]

Yafuso et al.

[11] Patent Number: 5,345,932
[45] Date of Patent: Sep. 13, 1994

[54] METHOD AND SYSTEM FOR MONITORING OF BLOOD CONSTITUENTS IN VIVO

[75] Inventors: Masao Yafuso, El Toro, Calif.; Laurence A. Harker, Atlanta, Ga.

[73] Assignee: Minnesota Mining and Manufacturing Company, St. Paul, Minn.

[21] Appl. No.: 5,765

[22] Filed: Jan. 15, 1993

Related U.S. Application Data

[62] Division of Ser. No. 820,565, Jan. 14, 1992, Pat. No. 5,195,963, which is a division of Ser. No. 478,248, Feb. 9, 1990, abandoned.

[51] Int. Cl.$^5$ .............................................. A61B 5/00
[52] U.S. Cl. ..................................... 128/637; 128/692
[58] Field of Search ................. 604/4, 5, 181, 265, 604/49; 128/632–634, 637, 666, 670, 760, 768, 772, 692, 833

[56] References Cited

U.S. PATENT DOCUMENTS

| | | |
|---|---|---|
| 3,512,517 | 11/1964 | Kadish et al. |
| 3,529,591 | 9/1970 | Schuette . |
| 3,674,013 | 7/1972 | Polanyi ................ 128/634 |
| 3,807,390 | 4/1974 | Ostrowski et al. ........ 128/634 |
| 3,814,081 | 5/1974 | Mori ....................... 128/634 |
| 3,866,599 | 2/1975 | Johnson ................. 128/634 |
| 3,878,830 | 4/1975 | Bicher .................... 128/635 |
| 3,983,864 | 10/1976 | Sielaff et al. .............. 128/632 |
| 4,016,864 | 4/1977 | Sielaff et al. .............. 128/632 |
| 4,050,450 | 9/1977 | Polanyi et al. ............ 128/634 |
| 4,221,567 | 9/1980 | Clark et al. ............... 23/230 B |
| 4,444,198 | 4/1984 | Petre ...................... 128/673 |
| 4,478,222 | 10/1984 | Koning et al. ............ 128/632 |
| 4,535,786 | 8/1985 | Kater ..................... 128/160 |
| 4,573,968 | 3/1986 | Parker .................... 604/67 |
| 4,585,007 | 4/1986 | Uchigaki et al. .......... 128/632 |
| 4,736,748 | 4/1988 | Nakamura et al. ........ 128/632 |
| 4,774,955 | 10/1988 | Jones .................... 128/632 |
| 4,830,013 | 5/1989 | Maxwell ................. 128/637 |
| 4,841,974 | 6/1989 | Gumbrecht et al. ....... 128/635 |
| 4,909,799 | 3/1990 | Thulesius et al. ......... 604/265 |
| 4,938,873 | 7/1990 | Rossi .................... 604/5 |
| 4,955,878 | 9/1990 | See et al. ................ 604/181 |

FOREIGN PATENT DOCUMENTS

| | | | |
|---|---|---|---|
| 0276535 | 5/1987 | European Pat. Off. | ........ A61B 5/14 |
| 0259951 | 7/1987 | European Pat. Off. | ...... G01N 21/64 |
| 0273258 | 12/1987 | European Pat. Off. | ........ A61B 5/00 |

OTHER PUBLICATIONS

UpJohn Brochure Prostin VR Pediatric ® brand of alprostadil sterile solution.
Optical Fluorescence and Its Application to an Intravascular Blood Gas Monitoring System, John L. Gehrich, IEEE Transactions on Bio–Medical Engineering vol. BME No. 2, Feb. 1986.
J. Fareed et al., "Pharmacologic Profiling of Defibrotide in Experimental Models," Seminars in Thrombosis and Hemostasis–Supplement, vol. 14, pp. 27–37 (1988).
O. N. Ulutin, "Clinical Effectiveness of Defibrotide in Vaso–Occlusive Disorders and its Mode of Actions," Seminars in Thrombosis and Hemostasis–Supplement, vol. 14, pp. 58–63 (1988).
U. Cornelli et al., "Defibrotide; An Overview of Clinical Pharmacology and Early Clinical Studies," Seminars in Thrombosis and Hemostasis–Supplment, vol. 14, pp. 64–70 (1988).

*Primary Examiner*—John D. Yasko
*Assistant Examiner*—Michael Rafa
*Attorney, Agent, or Firm*—Gary L. Griswold; Walter N. Kirn; Dale E. Hulse

[57] ABSTRACT

A method for determining the concentration of a constituent of blood employing a sensor in or near a catheter in a blood vessel for producing a signal related to the concentration of the constituent of blood is disclosed. The improvement comprises obtaining the signal while at least one of the following is present in the blood vessel: (1) an added vasodilator component and/or vasodilation promotor in an amount effective to reduce the vasoconstriction caused by the presence of the catheter in the blood vessel and (2) an added platelet/white cell inhibitor component and/or a platelet/white cell deactivation promotor in an amount effective to reduce the platelet and/or white cell activation caused by the presence of the catheter in the blood vessel.

32 Claims, 3 Drawing Sheets

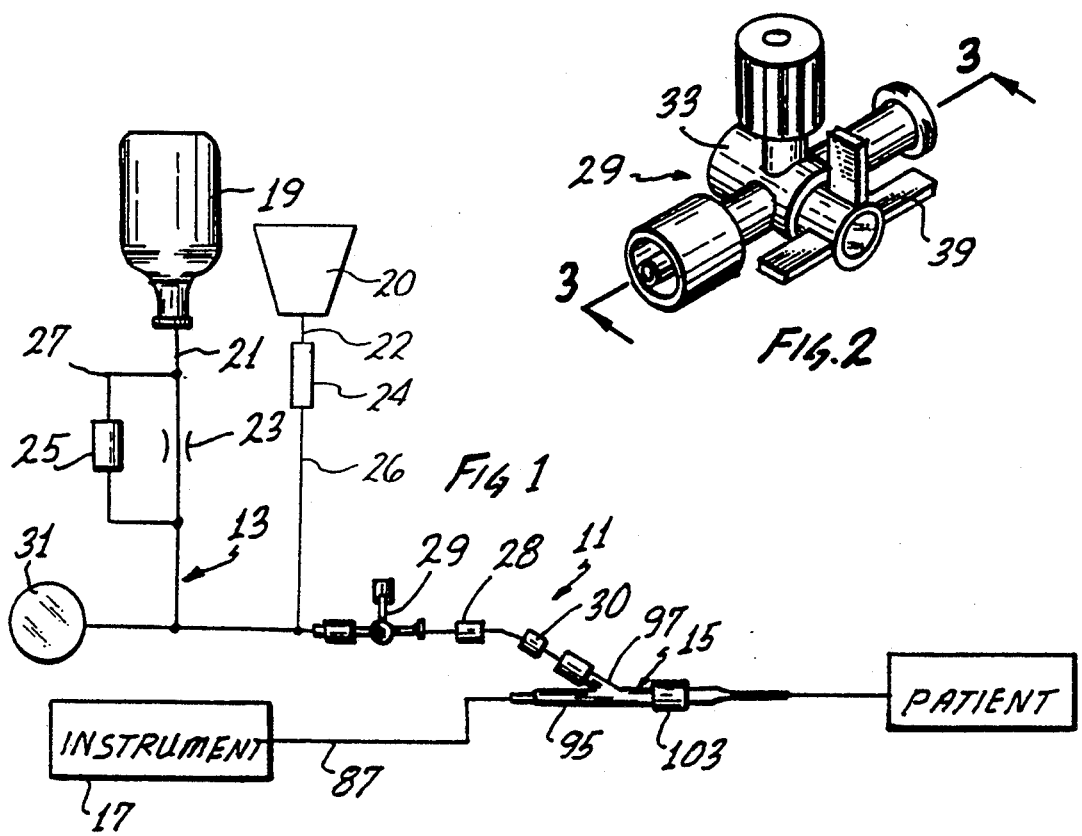
Fig. 1
Fig. 2
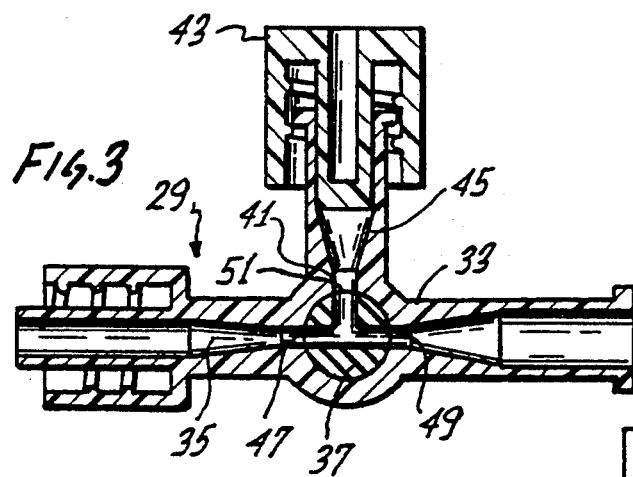
Fig. 3
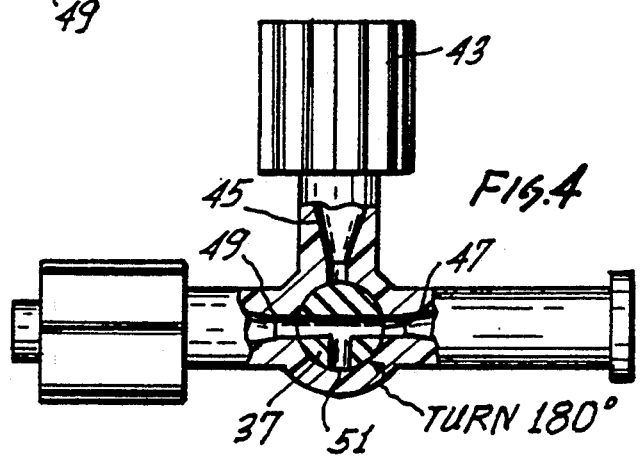
Fig. 4

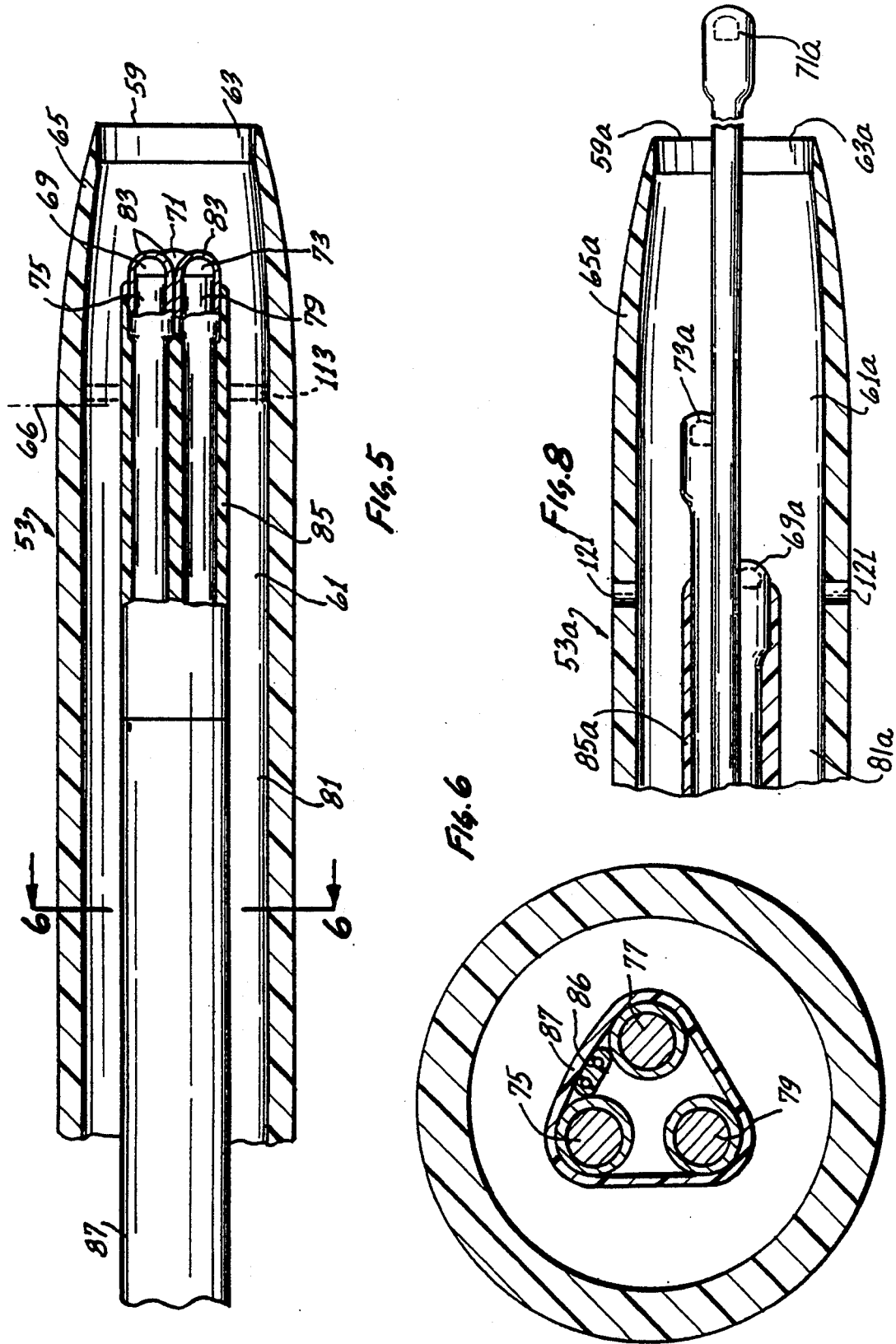

METHOD AND SYSTEM FOR MONITORING OF BLOOD CONSTITUENTS IN VIVO

The present application is a division of U.S. application Ser. No. 07/820,565, filed Jan. 14, 1992 U.S. Pat. No. 5,195,963, which application is a division of U.S. application Ser. No. 07/478,248, filed Feb. 9, 1990 abandoned.

BACKGROUND OF THE INVENTION

It is often necessary or desirable to measure various blood constituents, such as blood gases, pH, other electrolytes and glucose. This can be accomplished in real time using various sensors, for example electrochemical sensors and fluorescent sensors. This can be accomplished in an extracorporeal blood loop as shown in Cooper U.S. Pat. Nos. 4,640,820 and in vivo as disclosed in Lubbers et al Reissue No. 31,879. For in vivo sensing, a probe or catheter carrying an appropriate sensor is inserted into a blood vessel of the patient.

One of the most important gases that needs to be sensed is oxygen. One problem with in vivo oxygen sensing is that the readings obtained for the concentrations of oxygen tend to vary over an unacceptably wide range when compared with the results obtained using conventional laboratory techniques for measuring the concentration of oxygen. Carbon dioxide concentrations and pH determinations also tend to vary relative to values obtained using conventional laboratory techniques. It has been found that such deviations are in many cases unacceptably large so that the reliability of the in vivo measuring system is called into question.

SUMMARY OF THE INVENTION

At least one feature of the invention is based, in part, upon the recognition and discovery of the reasons why unacceptable results were often obtained in the in vivo system. Specifically, it has been discovered that blood sampled by sensors in fluid communication with a patient's blood vessel, particularly by sensors located in or in fluid communication with catheters placed in a patient's blood vessel, especially an artery, can have constituent concentrations which differ significantly from those of the blood elsewhere in the blood vessel, e.g., of freshly arterialized blood. Further, it has been discovered that one cause of these blood constituent concentration differences is the presence of the cannula or the catheter itself. Without wishing to limit the invention to any particular theory of operation, it is believed that the insertion of the catheter into the blood vessel and/or the presence of the catheter in the blood vessel trigger responses by vascular and adjacent tissue, e.g., vasoconstriction; and activation of platelets and white cells. This increased activity causes a lowering of blood oxygen concentration and blood pH, and an increase in blood carbon dioxide concentration. These changes are aggravated if the blood flow drops. Platelets and white cells can be activated because of the catheter insertion wound, by damage to endothelial cells caused by the catheter, needle, guidewire, etc., and/or simply by blood contact with the foreign surfaces of the catheter and/or sensors. Blood flow can be decreased by vasoconstriction induced by factors released by the injury response and/or by various of the activation processes referred to above.

Having recognized these problems, this invention solves these problems by inhibiting such responses and/or such activation. In particular, the present invention involves obtaining signals indicative of the concentration of a constituent of blood while at least one of the following is present in the blood vessel: (1) an added vasodilator component and/or an added vasodilation promotor; and (2) an added platelet/white cell inhibitor component and/or an added platelet/white cell deactivation promotor. As used herein the term "component" refers to a substance which acts directly to reduce vasoconstriction and/or to reduce platelet and/or white cell activation. The term "promotor" refers to a substance which acts to effect the production, preferably the endogenous production, of a vasodilator component and/or a platelet/white cell inhibitor component. Only one of these substances need be present to provide beneficial results. The presence of one or more of these substances in an effective amount allows one to more accurately monitor the concentration of the blood constituent of interest.

The sensor or sensing element is in direct fluid communication with, and preferably is located in, the blood vessel where the blood to be analyzed is located. That is, there is a direct or open fluid path between the interior of the blood vessel and the sensor. In one useful embodiment, the sensor is located in the catheter in the blood vessel. The catheter has an opening to provide fluid communication between the interior of the blood vessel and the interior of the catheter, preferably a distal opening at the distal end of the catheter. One or more radial apertures may be provided in addition to the distal opening, if desired. Alternately the sensor or sensing element can be passed through the catheter and extend out of, e.g., out of an opening at the distal end of, the catheter into the blood vessel.

The sensor can be mounted in any desired way. One useful system includes a probe-catheter assembly which comprises a probe including at least one sensor for sensing a constituent of blood and providing a signal in response thereto and elongated transmission means for transmitting the signal from the sensor proximally. The sensor is preferably carried by a distal portion of the transmission means. The assembly also includes the catheter which has a lumen extending therethrough, a proximal end, a distal end and a distal opening at the distal end.

When utilizing a probe-catheter assembly of this type, the catheter can be used to keep the sensor from contacting the wall of the vessel. This can be advantageously accomplished by attaching the probe to the catheter such that the sensor of the probe is within the lumen of the catheter and adjacent the distal opening of the catheter. With this construction, the sensor is shielded from the wall of the vessel. Alternately, the sensor or sensors of the probe can extend out of the distal opening of the catheter.

An effective amount of an added vasodilator component vasodilation promotor, platelet/white cell inhibitor component and/or platelet/white cell deactivation promotor is present in the blood vessel at the time a signal in response to the blood constituent is obtained from or provided by the sensor. It has been found that the presence of an added vasodilator component and/or vasodilation promotor acts to reduce the vasoconstriction, e.g., the degree of vasoconstriction, caused by the presence of the catheter and/or sensor, in particular the probe-catheter assembly, in the blood vessel. The presence of an added platelet/white cell inhibitor component and/or platelet/white cell deactivation promotor acts to reduce the platelet and/or white cell activation e.g., the degree of platelet and/or white cell activation, caused by the presence of the catheter and/or sensor, in particular the probe-catheter assembly, in the blood vessel. Ultimately, the presence of one or more of these added substances leads to more accurate blood constituent determinations, e.g., determinations which more accurately reflect the true concentration of the constituent of interest in the blood in the blood vessel.

Such added substance or substances may be introduced into the blood vessel in any desired way. For example, such substance or substances may be taken orally or may be injected into the vascular system. Because the catheter or probe-catheter assembly is often located in one localized area of the vascular system it is preferred that the substance or substances be introduced into the blood vessel in such a manner that not all of the patient's vascular system is affected. More preferably, such substance or substances substantially affect only a limited portion of the patient's vascular system. Thus, the patient's natural response to injury and internal bleeding in other parts of his/her body are substantially unaffected by the presence of the presently useful substances in the blood vessel.

One particularly useful approach to introducing the substance or substances into the blood vessel is to do so through the catheter itself. This embodiment provides the substance or substances at the desired location. Also, by controlling the amount of such substance or substances that is introduced, one can reduce, and even substantially prevent, the effect of the substance or substances on the patient's vascular system away from the localized area of concern where the catheter, sensor or probe-catheter assembly is located.

Such substance or substances may be added to the anti-clotting solution normally introduced into the patient's vascular system through the catheter. This addition may be to the anti-clotting solution in bulk. Alternately, the substance or substances may be injected through the catheter independently of the anti-clotting solution, using a separate pumping device, such as an infusion pump.

Another approach to reducing the generalized effect of such substance or substances is to choose a substance or substances which have relatively short effective half lives. In other words, substance or substances to be chosen become only half as effective after a relatively short period of time in the patient's vascular system. Thus, by selecting such relatively short effective half-life substances, one can obtain useful results at the localized area of concern without having an unwanted effect on the patient's vascular system, in general. Particularly useful substances have effective half-lives in the range of about 0.1 minutes to about 5 minutes. Substances which lose at least about 50%, and preferably at least about 90%, of their effectiveness in the time it takes a patient's blood to make one pass through the patient's cardiovascular system are especially useful.

Any suitable vasodilator component and platelet/white cell inhibitor component may be employed provided that it functions as described herein. In one useful embodiment, a single compound or substance functions as both the vasodilator component and the platelet/white cell inhibitor component. A particularly useful group of combination vasodilator components/platelet/white cell inhibitor components includes prostaglandin $E_1$ (alprostadil) (hereinafter referred to as $PGE_1$), analogs of $PGE_1$, prostaglandin $E_2$ (hereinafter referred to as $PGE_2$), analogs of $PGE_2$, prostacyclin $I_2$ (hereinafter referred to an $PGI_2$), analogs of $PGI_2$ and mixtures thereof. An especially preferred combination vasodilator component/platelet/white cell inhibitor component is selected from $PGE_1$, synthetic analogs of $PGE_1$ and mixtures thereof.

$PGE_1$ is currently used to treat certain neonates with congenital heart defects. For such treatment, the Up-John Company sells a $PGE_1$ sterile solution, under the trademark Prostin VR Pediatric, which includes 500 micrograms of $PGE_1$ per milliliter of solution. The recommended dosage for this use with neonates is 0.01 micrograms per kilogram of body weight per minute or higher.

For the present purpose, the dosage of the particularly useful vasodilator component/platelet/white cell inhibitor component is preferably less than the dosage of $PGE_1$ used to treat neonates, as described above. The more preferred dosage for use in the present invention is in the range of about 1 pico ($10^{-12}$) grams to about 100 pico grams per kilogram of body weight per minute.

$PGE_1$, $PGE_2$ and $PGI_2$ are naturally occurring substances and are found in humans. $PGE_1$, $PGE_2$ and $PGI_2$ can also be synthetically produced. In any event, an added increment or dose of one or more of these substances is needed to effect the desired response, as described herein. As used herein, the term "analog" of one of these substances refers to any substance which has substantially similar compositional and/or functional characteristics, preferably both substantially similar compositional and functional characteristics, as does the naturally occurring substance for which it is an analog. Preferably, the presently useful synthetic analogs are synthetically produced.

Any suitable vasodilation promotor and/or platelet/white cell deactivation promotor may be employed provided that it functions as described herein, without wishing to limit the invention to any particular theory of operation, it is believed that these promotors have the following effects. The presence of vasodilation promotor is believed to do at least one of the following in the blood vessel: (1) effect endogenous production of vasodilator component; and (2) inhibit endogenous production of vasoconstrictor component. The presence of platelet/white cell deactivation promotor is believed to do at least one of the following in the blood vessel: (1) effect endogenous production of platelet/white cell inhibitor component; and (2) inhibit endogenous production of platelet/white cell activator component.

In one particularly useful embodiment, a single compound or substance functions as both the vasodilation promotor and the platelet/white cell deactivation promotor. A particularly useful group of combination vasodilation promotors/platelet/white cell deactivation promotors are those selected from defibrotide, analogs of defibrotide and mixtures thereof.

An anti-clotting solution, such as a heparinized saline solution, is preferably introduced into the catheter lumen from a solution-introducing system. The solution may be resident in the lumen, i.e., have no net flow into the vessel, but preferably it flows at a very low rate, such as 1 to 8 milliliters per hour, through the lumen and out through the distal opening of the catheter into the blood stream in the vessel.

If the sensor or sensors are located in the catheter, an "interface" may be envisioned as existing between the blood and the material, i.e., the anti-clotting solution and vasodilator component, vasodilation promotor, platelet/white cell inhibitor component, and/or platelet/white cell deactivation promotor, being introduced through the catheter. Theoretically, the interface could be a plane that simply divides the blood from the material. However, in reality, the interface is a zone which has some axial length and which contains gradient concentrations of both the blood and the material. Thus, the interface divides a zone of substantially all blood from a zone containing substantially all material being introduced.

By moving the interface back and forth in the lumen, the sensor can be exposed to blood for at least a portion of time that the interface is moving. This exposure must be sufficient to enable the sensor or sensors in the catheter to provide an accurate signal related to the blood constituent of interest.

The movement of the interface back and forth in the lumen may move the interface over the sensor. However, the sensors, and in particular the oxygen sensor, can tolerate some exposure to the mixture of the material being introduced and blood in the interface without providing erroneous readings.

Movement of the interface to bathe the sensor within the lumen in blood can be brought about in different ways. For example, the interface may be moved by varying the delivery pressure and/or volume of the material being introduced or providing the introducing system with a volume oscillator and allowing the volume oscillator to move the interface. The volume oscillator may, for example, take the form of a syringe which, in effect, expands and contracts the volume of the introducing system to move the blood back and forth in the lumen without creating a net or average flow in either direction.

Another technique for moving blood back and forth in the lumen, which also enables expansion and contraction of the volume of the introducing system, includes providing the introducing system with some compliance and allowing pressures generated by the patient's heartbeats to move the interface. Consequently, blood is forced to enter the distal opening of the catheter as the blood pressure rises with each beat of the heart. Thus, the interface is caused to flow back and forth in the lumen with the pulsating blood pressure. As a result, the sensor within the lumen is bathed by the back and forth or tidal movement of the blood and can adequately sense and measure the blood constituents of interest.

The compliance of the introducing system may be the natural compliance of the tubing and components of the system and/or a compliant element may be added to the system to provide the desired degree of elasticity. The compliant element can be of virtually any construction and may be, or include for example, a compressible fluid, such as air, a membrane, a bellows, etc. The compliance of the introducing system may be varied to obtain the results desired. For example, if the compliance of the introducing system is to be used to obtain, or to assist in obtaining, the tidal action, the introducing system and the catheter may have a combined total compliance sufficient to provide a volume exchange of at least 10 microliters with a system comprised of a 20-gauge catheter and 0.022 inch diameter probe.

When the sensor or sensors are located outside the catheter in the blood vessel, the concern with the blood/material being introduced interface and moving this interface are substantially eliminated. In this configuration, the sensor or sensors in the blood vessel are substantially continuously exposed to blood sufficiently to provide for useful constituent concentration measurements. Thus, no added compliance of the solution introducing system is necessary.

It may be necessary or desirable to take the patient's blood pressure through the lumen of the catheter while the blood constituents are being sensed. The added compliance, if any, of the introducing system may be sufficient to undesirably alter the blood pressure reading taken through the lumen of the catheter. Accordingly, the present invention provides, as an option, for selectively nullifying the ability of the compliant element to allow expansion and contraction of the volume of the introducing system. For example, the nullifying means may control expansion or adjustably limit movement of a membrane or bellows or it may selectively switch the compliant element into, and out of, communication with the lumen of the catheter. In this latter event, the compliant element would normally be in communication with the lumen to provide, or assist in providing, the desirable tidal action for sensing of the blood constituents of interest. However, just prior to taking a blood pressure reading, the action of the compliant element can be switched out of the introducing system so that it cannot affect the blood pressure reading taken through the lumen of the catheter. The switching means may take any form that will accomplish this function and may be, for example, a valve.

The probe may carry one or more sensors depending upon the number of blood constituents of interest. These sensors can be of any type, such as electro-chemical, that is suitable for sensing the constituent of interest; however, optical sensors are preferred, and fluorescent sensors are considered optimum. Although multiple sensors could be provided to sense the same blood constituent, preferably, each sensor senses a different blood constituent. In a preferred construction, the transmission means includes an optical fiber for each of the sensors, with the sensor being located on the distal end of the associated optical fiber. The sensors provide signals related to the associated blood constituent of interest, and such signals may be used or processed continuously, intermittently or on demand to provide readings indicative of the blood constituents of interest.

A conventional catheter usable with the invention has a standard lead-in taper, i.e., the cross-sectional area of the lumen reduces toward the distal opening in a zone closely adjacent the distal opening. The presence of the probe in this tapered zone tends to reduce the remaining open area of the lumen to the extent that the monitoring of blood pressure through the lumen is adversely affected. One approach to this problem is to position the sensors at different longitudinal locations relative to the longitudinal axis of the catheter. In the specific case of utilizing an optical fiber for each sensor, the optical fibers terminate distally at staggered locations. Consequently, not all of the sensors are located in the tapered zone, and a larger open area of the tapered zone remains for pressure sensing.

The invention, together with additional features and advantages thereof, may best be understood by reference to the following description taken in connection with the accompanying illustrative drawings.

BRIEF DESCRIPTION OF THE DRAWINGS

FIG. 1 is a schematic view of an assembly for the in vivo measurement of blood constituents of interest.

FIG. 2 is a perspective view of one form of valve usable in the assembly of FIG. 1.

FIG. 3 is an axial sectional view through the valve with the compliant element being in communication with the conduit leading to the lumen of the catheter.

FIG. 4 is an elevational view partially in section and similar to FIG. 3 with the compliant element being out of communication with the conduit.

FIG. 5 is an enlarged fragmentary sectional view of the distal region of one form of probe and catheter usable in the assembly of FIG. 1.

FIG. 6 is an enlarged sectional view taken generally along line 6—6 of FIG. 5.

FIG. 8 is a sectional view similar to FIG. 5 showing an alternate construction of the distal region of the probe.

DETAILED DESCRIPTION

Figure 7:
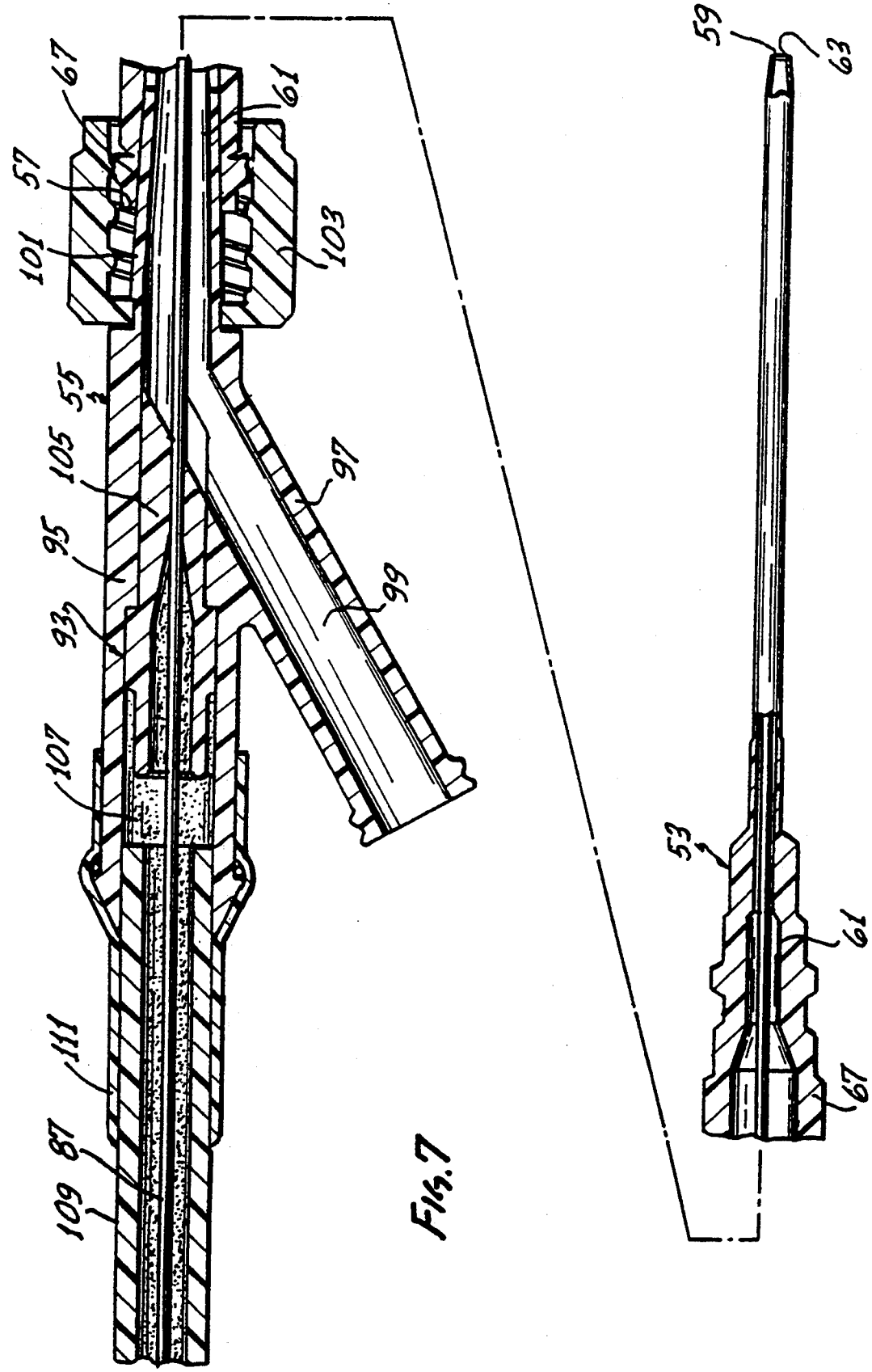
FIG. 7 is a longitudinal sectional view through the probe-catheter assembly.

FIG. 1 shows an assembly 11 for the in vivo measurement of various blood constituents, and particularly the pH value (which is a measure of the H+ ion concentration in the blood) and the concentrations of oxygen and carbon dioxide. Although the assembly 11 can be of different constructions, in this embodiment it includes a solution introducing system 13 and a probe-catheter assembly 15. The assembly 11 may also include an instrument 17 for providing a readout of the blood constituents of interest.

Generally, the solution introducing system 13 introduces an appropriate anti-clotting solution, such as a heparinized saline solution, through the probe-catheter assembly 15 to the patient to keep the line leading to the patient's blood vessel in which the probe-catheter assembly 15 is located patent. In addition, a solution containing sufficient $PGE_1$, a vasodilator component and platelet/white cell inhibitor component, so as to provide the patient with about 20 pico grams to about 60 pico grams of $PGE_1$ per kilogram of body weight per minute is passed to the patient through the probe-catheter assembly. Although the solutions can be introduced in different ways, in the embodiment shown schematically in FIG. 1, the system 13 includes a pressurized source 19 of such anti-clotting solution, a conduit 21 leading from the source 19 to the probe-catheter assembly 15, a flow restrictor 23 to reduce the rate of flow through the conduit 21 to the desired drop rate, a flush valve 25 in a bypass 27 around the restrictor 23, a $PGE_1$ solution source 20, a conduit 22, an infusion pump 24 to control the flow of $PGE_1$ solution to a desired rate, a conduit 26 through which $PGE_1$ solution is passed to conduit 21, a stop cock 28, a four-way valve 29, a blood withdrawal site 30 and a pressure transducer 31. All of the components of the system 13 may be conventional, and the system 13 may include other components, if desired. As an alternative, the $PGE_1$ can be included with the anti-clotting solution in pressurized source 19. In this embodiment, there is no need for source 20, conduit 22, infusion pump 24 and conduit 26, thus providing a less complex system to operate. In the illustrated embodiment, which provides for very precise control of the amount of $PGE_1$ flowing into the patient, anti-clotting solution from the pressurized source 19 flows through the restrictor 23 at a relatively slow rate, such as 5 ml/hour. The flow of $PGE_1$ solution from source 20 is controlled by infusion pump 24 to maintain the desired amount of $PGE_1$ in the blood vessel in which the distal portion of probe-catheter assembly 15 is located. The solutions flow through the valve 29 and the probe-catheter assembly 15 to the patient's vascular system, preferably the patient's radial artery. If a more rapid flow rate from the source 19 is desired, as for example during priming, the flush valve 25 can be manually opened to provide a relatively high-rate flow path around the restrictor 23 in a conventional manner.

The four-way valve 29 may also be of conventional construction. As shown in FIG. 3, the valve 29 includes a valve body 33 having a passage 35 extending therethrough and forming a portion of the conduit 21, a rotatable valve element 37 in the passage 35 and a handle 39 (FIG. 2) for manually rotating the valve element 37. The valve body 33 has a leg 41, and a closure cap 43 is attached to the leg 41 to define, along with the leg, a chamber 45 in which a compliant element in the form of air is located. The valve element 37 has ports 47 and 49 for communicating with the conduit 21, and a port 51 which can communicate with the chamber 45 as shown in FIG. 3 or which can be sealed and out of communication with the conduit 21 and the chamber 45 as shown in FIG. 4. In this manner, the compliant element can be switched into, or out of, the system 13.

The pressure transducer 31 communicates with the conduit 21 and can measure the pressure therein. Accordingly, with the probe-catheter assembly 15 inserted into the vascular system of a patient, the pressure transducer 31 can provide blood pressure readings. By rotating the valve element 37 to the position of FIG. 4, the compliance of the air within the chamber 45 cannot affect the blood pressure readings provided by the transducer 31. The blood withdrawal site 30 is used for taking blood samples from the patient through the probe-catheter assembly 15. Preferably for this kind of compliant element, the stop cock 28 is located between the valve 29 and the site 30 so that, by closing the stop cock 28, the air in the chamber 45 cannot be withdrawn during a blood withdrawal procedure.

The probe-catheter assembly 15 includes a catheter 53 and a probe 55 (FIG. 7). The catheter 53 may be a conventional arterial catheter. As such, the catheter 53 may include a proximal end 57, a distal end 59, a lumen 61 extending axially, completely through the catheter and opening at a distal opening 63 at the distal end. The catheter 53 has a standard lead-in taper, i.e., a tapered zone 65, which extends from a reference plane 66 along the outer periphery of the catheter 53 to the distal end 59. The diameter of the lumen 61 also decreases distally throughout the tapered zone 65 as shown in FIG. 5. The tapered zone 65 may extend about 0.090 inch proximally of the distal end 59. The catheter 53 has an externally threaded coupling 67 at its proximal end.

The probe 55 may be of various different constructions, and in the embodiment illustrated, includes an oxygen sensor 69, a carbon dioxide sensor 71 and a pH sensor 73, with each of the sensors affixed to the distal ends of single optical fibers 75, 77, 79, respectively, (FIG. 6). In this embodiment, the sensors 69, 71 and 73 are fluorescent optical sensors, and they respond to the concentration of oxygen, the concentration of carbon dioxide and the pH value, respectively, to provide continuous optical signals indicative of the condition sensed. The optical fibers 75, 77 and 79 serve as transmission means for transmitting the signals from the associated sensors proximally. The probe 55 is of very small cross-sectional area so that it fits within the lumen 61 with an ample radial clearance 81 as shown in FIG. 5. Although as illustrated the sensors are located in the lumen 61 of catheter 53, one or more of such sensors can extend out of catheter 53, e.g., out of the opening 63 at the distal end 59 of catheter 53.

The particular design of the probe 55 forms no part of this invention because this invention is applicable to probes of various different constructions. Briefly, however, the sensors 69, 71 and 73 are attached to the distal ends of the associated optical fibers 75, 77 and 79 in any suitable manner, and each of the sensors and the associated fiber is separately encased in an inner overcoat 83 which, among other things, may assist in retaining the sensor on the end of the associated fiber. The overcoat 83 is, of course, permeable to the relevant blood parameters so that such parameter, or one related to it, can be sensed by the sensors. An outer overcoat 85 covers the inner overcoats 83 and a length of the fibers just proximally of the overcoats 83. Proximally of the overcoat 85, the optical fibers 75, 77 and 79 and a temperature-sensitive element, such as a thermocouple 86 (FIG. 6), are suitably encased within an appropriate sheath 87.

The probe 55 includes a "Y" fitting 93 at its proximal end as shown in FIG. 7. The optical fibers 75, 77 and 79 extend within the sheath 87 completely through one leg 95 of the "Y" fitting 93 to the instrument 17 as shown in FIG. 1. Another leg 97 of the fitting 93 has a passage 99 which communicates with the lumen 61, and more particularly, with the clearance 81 around the probe 55. The leg 97 is coupled to the conduit 21 of the system 13 as shown in FIG. 1. A third leg 101 of the "Y" fitting 93 carries a rotatable internally threaded coupling 103 for attaching the "Y" fitting of the probe 55 to the proximal end of the catheter 53 outside the cardiovascular system of the patient.

Although the details of the fitting 93 form no part of this invention, the sheath 87 may be guided in the leg 95 by a sleeve 105 and retained in position by potting 107. The sheath 87 extends within a flexible tube 109 suitably attached to the leg 95, and shrink tubing 111 is provided over the adjacent end portions of the fitting and the tube for strain relief.

As shown in FIG. 5, with the proximal end of the catheter 53 coupled to the probe 55 by the coupling 103, the probe 55 is within the lumen 61, and the sensors 69, 71 and 73 are within the lumen adjacent the distal opening 63. Accordingly, with the catheter within the cardiovascular system of the patient, such as in a radial artery, the catheter 53 keeps the sensors from contacting the wall of the blood vessel.

In use of the assembly 11, the catheter 53 is first inserted into the radial artery using conventional techniques. Next, the probe 55 is inserted into the lumen 61 and attached to the proximal end of the catheter 53 with the coupling 103. This properly positions the sensors 69, 71 and 73 within the lumen 61. In priming the solution introducing system 13 prior to connection to the probe 55 in the artery, a small quantity of air is trapped in the chamber 45. This can be accomplished, for example, with the valve element 37 in the position of FIG. 4, by filling the conduit 21 with solution from the source 19 with the closure cap 43 removed from the valve 29, and without allowing the solution to flow into the leg 41. The closure cap 43 is then affixed to the leg 41 to trap the air in the chamber 45, and then the rotatable valve element 37 is turned to the position shown in FIG. 3. The conduit 21 can then be connected to the probe 55. A number of other configurations and constructions can be employed to provide the desired system compliance. Further, no additional compliance may be needed, particularly if the sensors are located out of catheter 53, e.g., extend out of the distal end 59 of catheter 53.

When the embodiment illustrated in FIG. 5 is in use, the solutions from the sources 19 and 20 completely fill the lumen 61 around the probe 55. The solutions are provided under a pressure such that there is a slow flow of liquid from the lumen 61 into the patient's artery. This introduction of liquid through the lumen and into the artery results in an interface 113 adjacent the distal opening 63 which has some axial length and which includes both blood and the solutions from the sources 19 and 20. The interface 113 is a partition between essentially all blood distally of the interface and essentially all solutions from sources 19 and 20 proximally of the interface. The interface washes axially back and forth in a tidal action as a result of the rising and falling of the patient's blood pressure with each heartbeat. If the solution introducing system 13 were perfectly rigid, it would not be possible for the blood to force the solutions from sources 19 and 20 proximally within the lumen 61 because the solutions are essentially incompressible. However, the conduit 21 is typically in the form of flexible plastic tubing, which has some elasticity or compliance to allow some of this tidal action to occur. In addition, the illustrated embodiment of the invention is provided with a compliant element in the form of air within the chamber 45 which adds additional elasticity or compliance to the system 13. Consequently, the interface can flow back and forth to bathe the sensors 69, 71 and 73 in blood.

With this embodiment of the invention, the back and forth travel of the interface 113 is a function of the magnitude of the patient's blood pressure, the compliance of the solution-introducing system 13 and the delivery pressure of the solutions from sources 19 and 20. However, assuming that there is some net flow of the solution out of the distal opening 63, it would be necessary for at least the distal region of the interface 113 to travel distally as far as the distal opening, unless it is possible for some of the solutions to migrate through the blood and through the distal opening. Because the flow rate of solutions into the bloodstream is relatively low, the precise manner in which the solutions the patient's bloodstream and the exact extent of travel of the interface 113 is not known. However, utilizing the tidal action of the interface, it is possible to bathe the sensors 69, 71 and 73 in blood sufficiently so that accurate readings are obtained.

Sufficient $PGE_1$ is provided in and around probe-catheter assembly 15 and in the artery to effectively reduce the degree of vascular constriction, and platelet and white cell activation caused by the insertion and presence of the probe-catheter assembly 15 in the patient's radial artery. Ultimately the presence of this added $PGE_1$ allows blood constituent measurements which are more representative of the blood constituent values of freshly arterialized blood leaving the left ventricle of the heart. In other words, these measurements more closely relate to freshly arterialized blood relative to similar measurements obtained with no added $PGE_1$ present. Moreover, the nature of $PGE_1$, the manner in which it is introduced into the patient's radial artery and the concentration at which it is introduced into the patient's radial artery allow for this beneficial localized effect to occur without substantially detrimentally affecting the patient's vascular system or blood supply in general.

FIG. 8 shows another embodiment of this invention which is identical to the embodiment of FIGS. 1–7 in all respects not shown or described herein. Portions of the embodiment of FIG. 8 corresponding to portions of the embodiment of FIGS. 1–7 are designated by corresponding reference numerals followed by the letter "a".

The primary differences between the embodiment of FIG. 8 and FIGS. 1–7 is that the sensors 69a, 71a, and 73a are at different longitudinal positions relative to the lumen 61a, the sensors 71a and 73a project farther from the overcoat 85a, with sensor 71a extending out of the distal opening 63a, and there are a plurality of radial apertures 121 in the catheter 53a leading from the lumen 61a adjacent the distal opening 63a of the catheter. In this embodiment, each of the three sensors terminates at a different axial position relative the lumen 61a, and with this construction, the total cross-sectional area of the probe 55a reduces in step-wise fashion from the distal end of the sensor 71a proximally. Consequently, not all of the sensors pass through the tapered zone 65a, and a larger cross-sectional area of the tapered zone remains open for pressure sensing via the pressure transducer 31 shown in FIG. 1.

In the construction of FIG. 8, preferably the carbon dioxide sensor 71a is the most distal sensor, and the oxygen sensor 69a is the most proximal. The reason for this is that carbon dioxide is the most sensitive to being even partially out of the blood. The sensitivity of the pH sensor 73a is intermediate the sensitivity of the carbon dioxide sensor 71a and the oxygen sensor 73a and so is preferably located intermediate these sensors.

The radial apertures 121 are preferably located proximally of the sensor 73a for the purpose of allowing blood and the solutions from the lumen 61a to flow out of the apertures. One or more of these apertures may be provided, and in the embodiment of FIG. 8, two of the apertures are shown. Of course, the apertures 121 may be distributed in axially spaced relationship, as well as circumferentially spaced relationship, along the catheter 53a. The apertures 121 may also be used in the embodiment of FIGS. 1–7, if desired.

In another embodiment, all of the sensors 69a, 71a and 73a extend through and out of the distal opening 63a of the catheter, as does sensor 71a in FIG. 8. In this embodiment, since the sensors are located in the blood in the artery, no added compliance or compliant member is needed since no blood-solution interface is involved and no tidal action is required. The $PGE_1$ from source 20 has been found to be effective to provide effective inhibition of vasoconstriction and effective inhibition of platelet and white cell activation to allow satisfactorily accurate measurements to be obtained even with the sensors directly in the blood vessel.

The $PGE_1$ in the description above can be supplemented with, or replaced by, defibrotide. Thus, in the case where the $PGE_1$ is replaced, defibrotide takes its place in source 20 or is included in the anti-clotting solution in pressurized source 19. This defibrotide is introduced into the patient in much the same way, using the same system, as described above with regard to $PGE_1$.

Sufficient defibrotide is provided in and around probe-catheter 15 and in the artery to effectively reduce the degree of vascular constriction, and platelet and white cell activation caused by the insertion and presence of the probe-catheter assembly 15 in the patient's radial artery. Ultimately the presence of this added defibrotide allows blood constituent measurements which are more representative of the blood constituent values of freshly arterialized blood leaving the left ventricle of the heart.

Although exemplary embodiments of the invention have been shown or described, many changes, modifications and substitutions may be made by one having ordinary skill in the art without necessarily departing from the spirit and scope of this invention.

What is claimed is:

1. A system for in vivo measurement of a constituent of a patient's blood comprising:
    a hollow catheter having an interior space and a distal end portion for being placed in a blood vessel of a patient, said distal end portion having an opening to allow blood to enter and exit said interior space of said catheter;
    a sensor for sensing the concentration of a constituent of the patient's blood and providing a signal in response thereto, said sensor being located in or near said interior space of said catheter;
    introduction means for introducing at least one of the following into said blood vessel: (1) at least one of a vasodilator component and a vasodilation promotor in an amount effective to reduce the vasoconstriction caused by the presence of said catheter in said blood vessel, thereby providing a more accurate determination of the concentration of the blood constituents, and (2) at least one of a platelet/white cell inhibitor component and a platelet/white cell deactivation promotor in an amount effective to reduce at least one of the platelet activation caused by the presence of said catheter in said blood vessel and the white cell activation caused by the presence of said catheter in said blood vessel, thereby providing a more accurate determination of the concentration of the blood constituent; and
    a quantity of at least one of said vasodilator component, said vasodilation promotor, said platelet/white cell inhibitor component and said platelet/white cell deactivation promotor associated with said introduction means.

2. The system of claim 1 wherein said sensor is located in said interior space of said catheter in said blood vessel.

3. The system of claim 1 which further comprises elongated transmission means for transmitting said signal from said sensor proximally.

4. The system of claim 2 wherein said sensor and said transmission means are received in said interior space of said catheter in said blood vessel.

5. The system of claim 2 wherein said transmission means extends distally of said catheter through said interior space of said catheter.

6. The system of claim 1 wherein said introduction means includes said catheter.

7. The system of claim 1 wherein said introduction means includes an infusion pump.

8. The system of claim 1 wherein said vasodilator component is also said platelet/white cell inhibitor component.

9. The system of claim 1 wherein said added vasodilator component is selected from the group consisting of prostaglandin $E_1$, analogs of prostaglandin E1, prostaglandin $E_2$ analogs of prostaglandin $E_2$, prostacyclin $I_2$, analogs of prostacyclin $I_2$ and mixtures thereof.

10. The system of claim 1 wherein said vasodilator component is selected from the group consisting of prostaglandin $E_1$, analogs of prostaglandin E1 and mixtures thereof.

11. The system of claim 1 wherein said vasodilation promotor is also said platelet/white cell deactivation promotor.

12. The system of claim 1 wherein said vasodilation promotor is selected from the group consisting of defibrotide, analogs of defibrotide and mixtures thereof.

13. The system of claim 1 wherein said sensor includes an optical indicator.

14. The system of claim 1 wherein said sensor includes a fluorescence indicator.

15. The system of claim 1 wherein said constituent of blood is selected from oxygen, carbon dioxide, $H^+$, glucose and other electrolytes.

16. The system of claim 1 wherein said sensor is a component of a probe which includes at least one other sensor for producing a signal related to the concentration of another constituent of blood.

17. The system of claim 1 wherein said elongated transmission means comprises an optical fiber and said sensor includes an optical indicator.

18. The system of claim 17 wherein said optical indicator is a fluorescence indicator.

19. A system for the in vivo measurement of a constituent of a patient's blood comprising:

a sensor for sensing the concentration of a constituent of interest of a patient's blood and providing a signal in response thereto, said sensor being located in a blood vessel of said patient;

introduction means for introducing at least one of the following into said blood vessel: (1) at least one of a vasodilator component and a vasodilation promotor in an amount effective to reduce the vasoconstriction caused by the presence of said sensor in said blood vessel, thereby providing a more accurate determination of the concentration of the blood constituent, and (2) at least one of a platelet/white cell inhibitor component and a platelet/white cell deactivation promotor in an amount effective to reduce at least one of: (A) the platelet activation caused by the presence of said sensor in said blood vessel, and (B) the white cell activation caused by the presence of said sensor in said blood vessel, thereby providing a more accurate determination of the concentration of the blood constituent; and a quantity of at least one of said vasodilator component, said vasodilation promotor, said platelet/white cell inhibitor component and said platelet/white cell deactivation promotor associated with said introduction means.

20. The system of claim 19 which further comprises elongated transmission means for transmitting said signal from said sensor proximally.

21. The system of claim 19 wherein said introduction means includes an infusion pump.

22. The system of claim 19 wherein said vasodilator component is also said platelet/white cell inhibitor component.

23. The system of claim 19 wherein said added vasodilator component is selected from the group consisting of prostaglandin $E_1$, analogs of prostaglandin E1, prostaglandin $E_2$ analogs of prostaglandin $E_2$, prostacyclin $I_2$, analogs of prostacyclin $I_2$ and mixtures thereof.

24. The system of claim 19 wherein said vasodilator component is selected from the group consisting of prostaglandin $E_1$, analogs of prostaglandin $E_1$ and mixtures thereof.

25. The system of claim 19 wherein said vasodilation promotor is also said platelet/white cell deactivation promotor.

26. The system of claim 19 wherein said vasodilation promotor is selected from the group consisting of defibrotide, analogs of defibrotide and mixtures thereof.

27. The system of claim 19 wherein said sensor includes an optical indicator.

28. The system of claim 19 wherein said sensor includes a fluorescence indicator.

29. The system of claim 19 wherein said constituent of blood is selected from oxygen, carbon dioxide, $H^+$, glucose and other electrolytes.

30. The system of claim 19 wherein said sensor is a component of a probe which includes at least one other sensor for producing a signal related to the concentration of another constituent of blood.

31. The system of claim 19 wherein said elongated transmission means comprises an optical fiber and said sensor includes an optical indicator.

32. The system of claim 31 wherein said optical indicator is a fluorescence indicator.

* * * * *

UNITED STATES PATENT AND TRADEMARK OFFICE
CERTIFICATE OF CORRECTION

PATENT NO. : 5,345,932
DATED : September 13, 1994
INVENTOR(S) : Masao Yafuso et al.

It is certified that error appears in the above-indentified patent and that said Letters Patent is hereby corrected as shown below:

Col. 12, line 28, claim 1, line 19, "constituents," should be --constituent,--.

Col. 12, line 49, claim 4, line 1, "2" should be --3--.

Col. 12, line 52, claim 5, line 1, "2" should be --3--.

Col. 12, line 64, claim 9, line 3, "E1" should be --$E_1$--.

Col. 12, line 65, claim 9, line 4, insert a comma after the first occurrence of "$E_2$".

Col. 13, line 1, claim 10, line 3, "E1" should be --$E_1$--.

Col. 13, line 21, claim 17, line 1, "1" should be --3--.

Col. 14, line 18, claim 23, line 3, "E1" should be --$E_1$--.

Col. 14, line 19, claim 23, line 4, insert a comma after the first occurrence of "$E_2$".

Col. 14, line 42, claim 31, line 1, "19" should be --20--.

Signed and Sealed this

Twenty-first Day of March, 1995

Attest:

BRUCE LEHMAN

*Attesting Officer*  *Commissioner of Patents and Trademarks*